US00PP18700P2

(12) United States Plant Patent
Utecht

(10) Patent No.: US PP18,700 P2
(45) Date of Patent: Apr. 1, 2008

(54) ***PELARGONIUM* PLANT NAMED 'GRADOSAL'**

(50) Latin Name: *Pelargonium×hortorum*
Varietal Denomination: Gradosal

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/506,075

(22) Filed: Aug. 17, 2006

(51) Int. Cl.
*A01H 5/00* (2006.01)

(52) U.S. Cl. ..... Plt./327
(58) Field of Classification Search ..... Plt./327
See application file for complete search history.

(56) References Cited

PUBLICATIONS

UPOV–ROM GTITM, Plant Variety Database, 2007/01, GTI Jouve Retrieval Software, Citation for Pelargonium 'Gradosal' and 'Fiv 281', 2 pages.*

Flora–Nova Pflanzen GmbH [online] [retrieved on Jul. 30, 2007]. Retrieved from the Internet: <http://www.top500.de/details/475.flora–nova_pflanzen_gmbh_germany.php> 2 pages.*

* cited by examiner

*Primary Examiner*—Kent Bell
*Assistant Examiner*—June Hwu
(74) *Attorney, Agent, or Firm*—Jondle & Associates, P.C.

(57) ABSTRACT

A new cultivar of *pelargonium* particularly characterized by having salmon-orange, double and stellar-type flowers, floriferous with medium-sized inflorescences, medium-green, fan-shaped foliage with distinct zonation, medium to tall, rounded, well-branched and vigorous plant habit and early flowering response, is disclosed.

1 Drawing Sheet

Genus and species: *Pelargonium×hortorum.*
Variety denomination: 'Gradosal'.

BACKGROUND OF THE NEW PLANT

The present invention comprises a new and distinct cultivar of *pelargonium,* botanically known as *Pelargonium× hortorum,* and hereinafter referred to by the cultivar name 'Gradosal'. The new cultivar is a product of a planned breeding program which had the objective of creating a range of new medium-sized varieties having orange, stellar-type flowers, stable flower color and medium-green foliage. 'Gradosal' was discovered as a seedling resulting from the cross of the female parent 'K99-4006-2' (unpatented), a proprietary *pelargonium* plant having pale-salmon, single-type flowers and the male parent 'K00-5035-12' (unpatented) a proprietary *pelargonium* plant having pink, double flowers.

The new cultivar was created in 2001 in Hillscheid, Germany and has been asexually reproduced repeatedly by vegetative cuttings Galdar, Gran Canaria, Spain, and Hillscheid, Germany over a four-year period. It has been found to retain its distinctive characteristics through successive asexual propagations. 'Gradosal' reproduces true to type in successive generations of asexual reproduction.

Plant Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when grown under normal horticultural practices in Hillscheid, Germany.

1. Salmon-orange, double and stellar-type flowers;
2. Floriferous with medium-sized inflorescences;
3. Medium-green, fan-shaped foliage with distinct zonation;

4. A medium to tall plant habit with vigorous growth;
5. A rounded and well-branched plant habit; and
6. An early flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of a 15-week-old, un-pinched plant grown from rooted cuttings, in 14-cm pots, and grown under greenhouse and outdoor conditions which approximate those generally used in commercial practice.

DESCRIPTION OF THE NEW CULTIVAR

The following detailed description sets forth the distinctive characteristics of 'Gradosal'. The data which define these characteristics were collected from asexual reproductions carried out in Hillscheid, Germany. The plant history was taken on 12-week-old, un-pinched plants in 12-cm pots in a greenhouse during late May. Color readings were taken under natural light in late May from flowers grown in the greenhouse. Color references are primarily to The R.H.S. Colour Chart of The Royal Horticultural Society of London (R.H.S.) (2001).

DETAILED BOTANICAL DESCRIPTION

Classification:

*Family.*—Geraniaceae.
*Botanical.*—*Pelargonium×hortorum.*
*Common name.*—Zonal geranium, stellar type.

Parentage:

*Female parent.*—'K99-4006-2', a proprietary *pelargonium* plant having pale-salmon, single-type flowers (unpatented).

*Male parent.*—'K00-5035-12', a proprietary *pelargonium* plant having pink, double flowers (unpatented).

Plant:

*Form.*—Shrub, self-branching, rounded shape.

*Branching habit.*—8 to 10 branches per plant.

*Height (measured from base of the stem to the tips of the branches, excluding the inflorescence, 9 weeks old).*—22.0 cm.

*Width (plant diameter, 9 weeks old).*—31.7 cm.

*Time to produce a finished flowering plant.*—Plants had an average of 0.8 opened inflorescences about 9 weeks after planting rooted cuttings in Hillscheid, Germany.

*Outdoor plant performance.*—Plants continuously flower; a count in late summer of 2005 in Hillscheid, Germany produced about 20 inflorescences per plant for 30-week-old plants.

Leaves:

*Arrangement.*—Alternate.

*Immature leaf color.*—Medium green. Upper surface: RHS 137C. Lower surface: RHS 138A.

*Mature leaf color.*—Upper surface: RHS 137C. Lower surface: RHS 137D.

*Zonation color.*—RHS 166A (brown) with a medium distinctness.

*Zonation diameter.*—Inner diameter of ring: 4.8 cm. Band or belt of zonation: 1.5 cm.

*Size.*—Length: 4.6 cm. Width: 9.6 cm.

*Shape.*—Semi-circular or flabellate with distinct lobes.

*Apex.*—Rounded, lobate (no leaf tip).

*Base.*—Truncate.

*Margin.*—Dentate.

*Texture.*—Upper surface is smooth, dull, and velvety and the lower surface is smooth (apart from the protruding veins) and covered with fine pubescence.

*Petioles.*—Color: RHS 138B (dull light-green). Length: 4.0 cm to 6.0 cm. Diameter: 0.2 cm. Texture: Pubescent.

Stems:

*Stem color.*—RHS 143C (light-green).

*Length.*—14 cm to 17 cm.

*Diameter.*—0.5 cm to 0.8 cm.

*Internode length.*—1.5 cm to 2.5 cm.

*Texture.*—Appear smooth but with slight, very short pubescence.

Inflorescence bud: (just before petals unfold).

*Shape.*—Elliptical.

*Size.*—Length: 1.4 cm. Width: 0.8 cm.

*Color of sepals.*—RHS 143C (light-green).

*Color of petals.*—RHS 41C.

Inflorescence:

*Inflorescence type.*—An umbel composed of 20 to 25 flowers.

*Umbel.*—Shape: Nearly semi-spherical but somewhat flatter. Diameter: 5.8 cm. Height (depth): 2.5 cm to 3.5 cm.

*Lastingness of umbel on the plant.*—About 16 days.

*Peduncle.*—Color: RHS 143B (grass-green). Length: 22.4 cm. Diameter: 0.3 cm to 0.4 cm. Texture: Pubescent.

*Pedicel.*—Color: Mainly RHS 176C or RHS 180C (reddish-brown) but partly RHS 143C (light-green). Length: 2.2 cm. Diameter: 0.15 cm. Texture: Covered with short glandular hair.

Corolla:

*Shape of corolla.*—Somewhat irregularly star-shaped, with the petals initially slanting upright and later are nearly horizontally-directed, appearing almost like ray-flowers.

*Form.*—Double.

*Diameter.*—2.6 cm.

*Depth.*—0.7 cm to 1.2 cm.

*Number of petals.*—12 to 16.

*Petaloids.*—Number: 1 to 3. Shape: Narrow, thread-like or band-like and sometimes twisted. Color: RHS 40A to RHS 40B.

*Lastingness of individual flowers on the plant.*—8 days at 18° C.

*Fragrance.*—None.

Petals:

*Shape.*—Elongated or elliptical.

*Apex.*—Acute.

*Base.*—Acute to acuminate.

*Margin.*—Entire or lobed, sometimes divided at tip.

*Texture.*—The upper surface is smooth, slightly glossy and the lower surface is glabrous.

*Upper petals.*—Length: 1.7 cm to 1.8 cm. Width: 0.3 cm to 0.5 cm. Color: Upper surface: RHS 43C. Lower surface: Near RHS 43D. Markings: Absent.

*Lower petals.*—Length: 1.5 cm to 1.6 cm. Width: 0.5 cm to 0.7 cm. Color: Upper surface: Between RHS 43C and RHS 43D. Lower surface: RHS 38A or RHS 43D and somewhat lighter toward the tips. Markings: Absent.

Sepals:

*Number.*—5.

*Color.*—RHS 143C (light-green) for both the upper and lower surfaces, and also RHS 144A for the lower side.

*Anthocyanin.*—Absent.

*Length.*—0.6 cm to 0.7 cm.

*Width.*—Largest upper sepal.—0.2 cm to 0.25 cm. Other sepals.—0.1 cm to 0.15 cm.

*Shape.*—Ligulate.

*Apex.*—Acute.

*Base.*—Fused.

*Margin.*—Entire.

*Texture.*—Short glandular hair and sparse long hairs on the lower surface and the upper surface is glabrous.

Reproductive organs:

*Androecium.*—Number of anthers: 1 to 5. Filament length: 0.5 cm. Filament color: RHS 155D (white) to RHS 41C at the upper end. Pollen color: RHS 28A (orange). Pollen amount: Moderate.

*Gynoecium.*—Pistil: Number: 1. Length: 0.5 cm to 0.6 cm. Stigma color: RHS 43B (salmon-red). Stigma shape: 5 to 6 lobed. Style color: RHS 43C (salmon-pink). Style length: 0.3 cm. Style shape: Filiform (filament-like), the lobes of the stigma are decurrent.

Fruit and seed set: No seed set observed.

Disease and insect resistance: No particular resistance or susceptibility has been observed.

COMPARISON WITH PARENTAL AND COMMERCIAL CULTIVARS

'Gradosal' differs from the female parent 'K99-4006-2' (unpatented) by having salmon-orange, double flowers, while 'K99-4006-2' has light-salmon, single flowers.

'Gradosal' differs from the male parent 'K00-5035-12' (unpatented) by having salmon-orange flowers, while 'K00-5035-12' has pink flowers.

'Gradosal' differs from the commercial variety 'Supernova' (unpatented) by having salmon-orange flowers, while 'Supernova' has light-pink flowers. In addition, 'Gradosal' has a more vigorous growth habit than 'Supernova'.

I claim:

1. A new and distinct cultivar of *pelargonium* plant as shown and described herein.

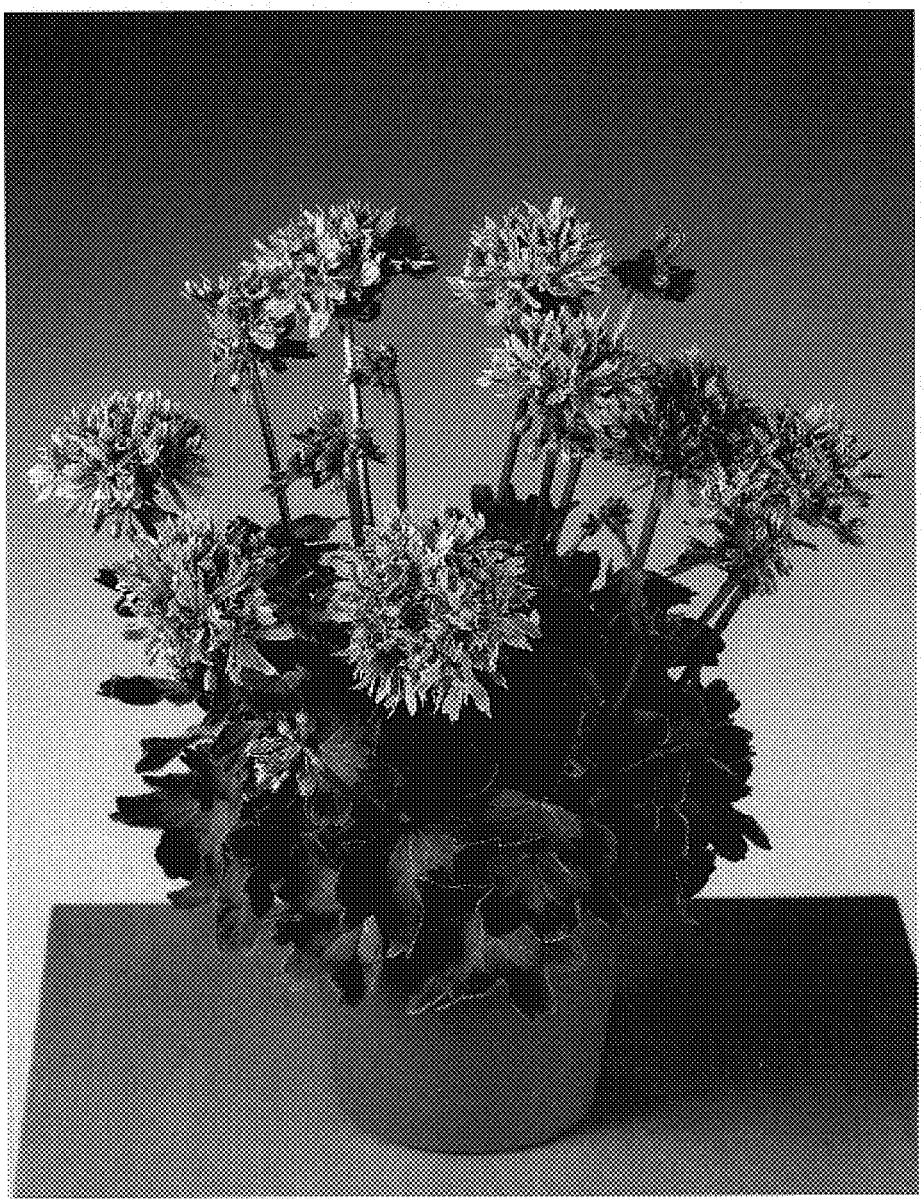

* * * * *